(12) United States Patent
Ando et al.

(10) Patent No.: US 12,023,320 B2
(45) Date of Patent: Jul. 2, 2024

(54) THERAPEUTIC AGENT FOR FATTY LIVER DISEASE

(71) Applicant: EA PHARMA CO., LTD., Tokyo (JP)

(72) Inventors: Ayatoshi Ando, Kawasaki (JP); Ippei Kawanishi, Tokyo (JP); Seiji Shiraishi, Kawasaki (JP); Harumi Tanaka, Kawasaki (JP); Yuki Saitou, Kawasaki (JP)

(73) Assignee: EA PHARMA CO., LTD., Tokyo (JP)

( * ) Notice: Subject to any disclaimer, the term of this patent is extended or adjusted under 35 U.S.C. 154(b) by 0 days.

(21) Appl. No.: 18/171,126

(22) Filed: Feb. 17, 2023

(65) Prior Publication Data

US 2023/0201163 A1 Jun. 29, 2023

Related U.S. Application Data

(63) Continuation of application No. PCT/JP2021/030099, filed on Aug. 18, 2021.

(30) Foreign Application Priority Data

Aug. 19, 2020 (JP) ................................ 2020-138703

(51) Int. Cl.
*A61K 31/40* (2006.01)
*A61P 1/16* (2006.01)

(52) U.S. Cl.
CPC ................ *A61K 31/40* (2013.01); *A61P 1/16* (2018.01)

(58) Field of Classification Search
CPC ................................... A61K 31/40; A61P 1/16
See application file for complete search history.

(56) References Cited

U.S. PATENT DOCUMENTS

| | | |
|---|---|---|
| 8,609,715 B2 | 12/2013 | Konishi et al. |
| 8,877,805 B2 | 11/2014 | Konishi et al. |
| 9,024,044 B2 | 5/2015 | Koshiba et al. |
| 9,115,107 B2 | 8/2015 | Konishi et al. |
| 9,227,949 B2 | 1/2016 | Koshiba et al. |
| 9,655,879 B2 | 5/2017 | Koshiba et al. |
| 2012/0283222 A1 | 11/2012 | Konishi et al. |
| 2014/0094489 A1 | 4/2014 | Suzuki et al. |
| 2016/0376248 A1 | 12/2016 | Takashita |
| 2016/0376249 A1 | 12/2016 | Yamada et al. |
| 2017/0281739 A1 | 10/2017 | Ilan |

FOREIGN PATENT DOCUMENTS

| | | | |
|---|---|---|---|
| WO | WO 2011/071048 A1 | 6/2011 | |
| WO | WO 2012/169579 A1 | 12/2012 | |
| WO | WO 2013/187533 A1 | 12/2013 | |
| WO | WO-2013187533 A1 * | 12/2013 | ............. A61K 31/19 |
| WO | WO 2015/137407 A1 | 9/2015 | |
| WO | WO 2015/137408 A1 | 9/2015 | |

OTHER PUBLICATIONS

Tarantino et al., "Non-alcoholic fatty liver disease: Further expression of metabolic syndrome", Journal of Gastroenterology and Hepatology, vol. 22, No. 3, pp. 293-303 (2007).*
International Search Report issued Oct. 12, 2021 in PCT/JP2021/030099 filed Aug. 18, 2021, 2 pages.
Toonen, Erik. J.M. et al., "Activation of Proteinase 3 Contributes to Nonalcoholic Fatty Liver Disease and Insulin Resistance" Molecular Medicine, 2016, vol. 22, pp. 202-214.
Chalasani, Naga. et al. "The Diagnosis and Management of Nonalcoholic Fatty Liver Disease: Practice Guidance From the American Association for the Study of Liver Diseases" HEPATOLOGY, 2018, vol. 67, pp. 328-357.
"Noncirrhotic Nonalcoholic Steatohepatitis With Liver Fibrosis: Developing Drugs for Treatment Guidance for Industry" U.S Department of Health and Human Services, 2018, 12 pages.
Japanese Office Action dated Feb. 10, 2023 in corresponding Japanese Patent Application 2022-543965 (with English translation).
Office Action dated Sep. 18, 2023, in corresponding European Patent Application No. EP 21858322.7.

* cited by examiner

*Primary Examiner* — Kevin E Weddington
(74) *Attorney, Agent, or Firm* — Oblon, McClelland, Maier & Neustadt, L.L.P.

(57) ABSTRACT

An object of the present invention is to provide a therapeutic agent for fatty liver diseases. The above object can be achieved by a therapeutic agent for a fatty liver disease, comprising a compound represented by the following formula (1):

(1)

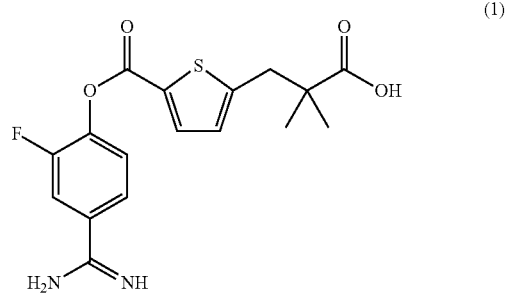

or a pharmaceutically acceptable salt thereof.

11 Claims, 4 Drawing Sheets

[FIG. 1A]
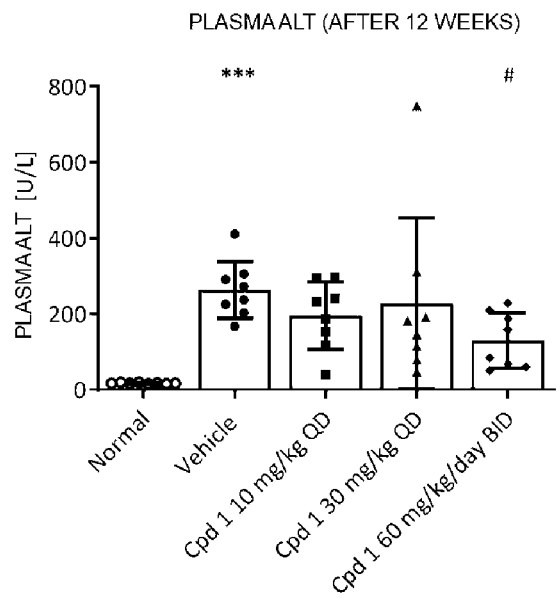
[FIG. 1B]
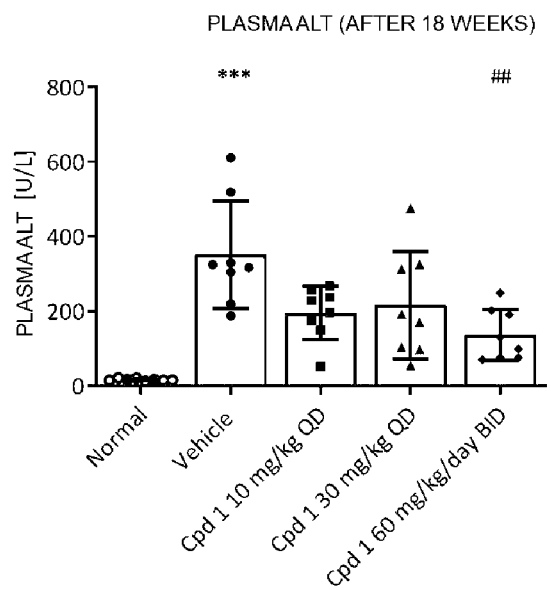

[FIG. 1C]
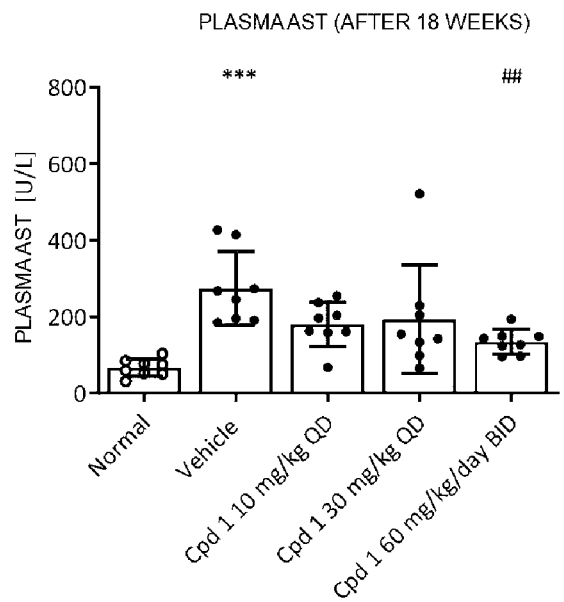
[FIG. 2]
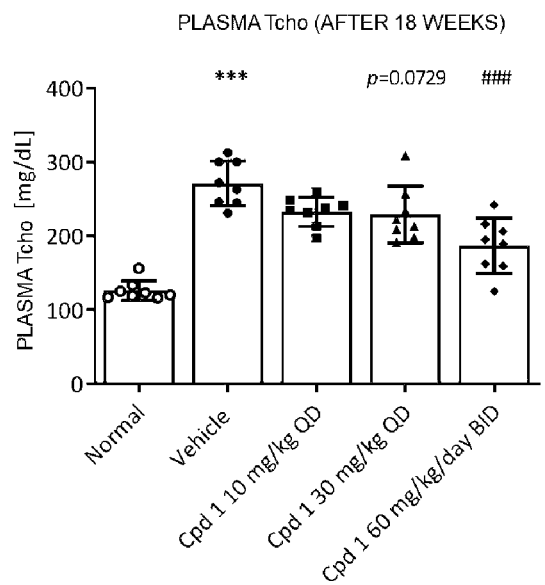

[FIG. 3]
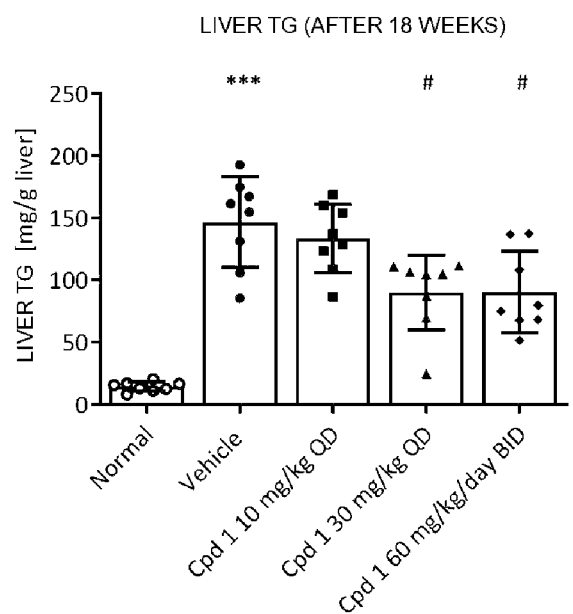

[FIG. 4]
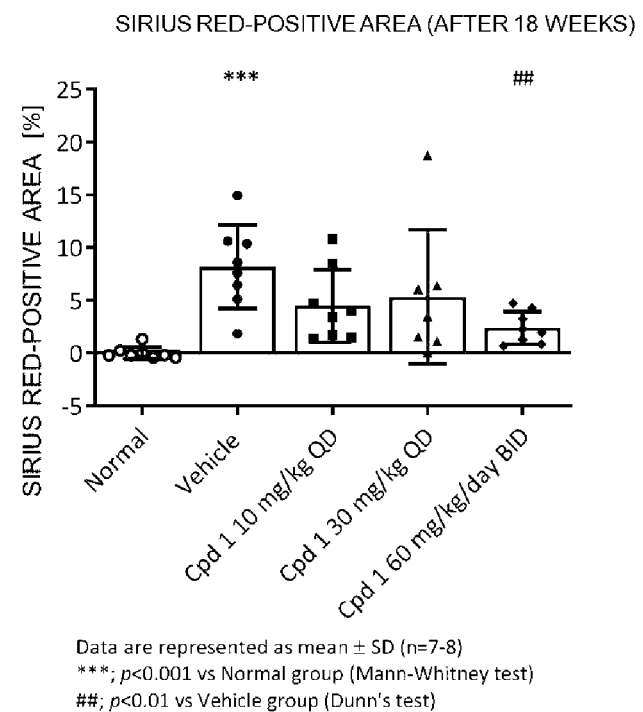
[FIG. 5]
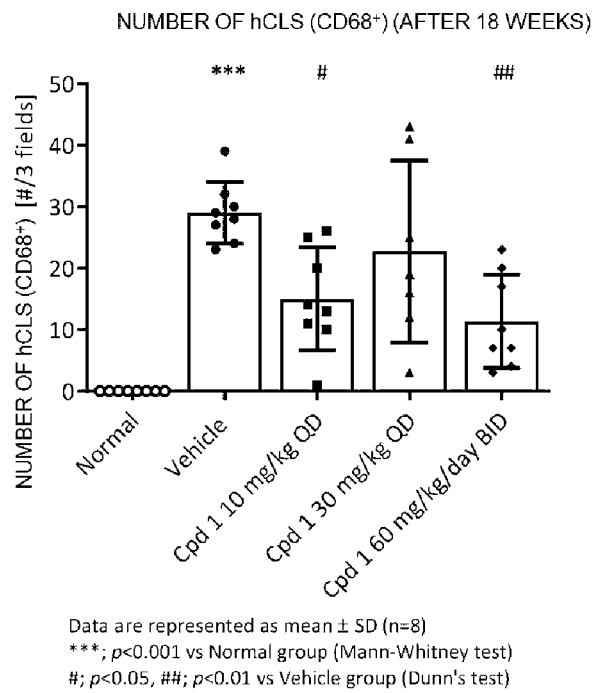

THERAPEUTIC AGENT FOR FATTY LIVER DISEASE

CROSS REFERENCE TO RELATED APPLICATIONS

This application is a continuation of PCT/JP2021/030099, filed on Aug. 18, 2021, the entire contents of which are incorporated herein by reference, and claims foreign priority to JP 2020-138703, filed on Aug. 19, 2020, the entire contents of which are incorporated herein by reference.

TECHNICAL FIELD

The present invention relates to a therapeutic agent for fatty liver diseases.

BACKGROUND TECHNOLOGY

Non-alcoholic fatty liver disease (NAFLD), which is one of fatty liver diseases, is a liver disease caused by the accumulation of excess lipids in the liver due to metabolic syndrome, such as obesity, diabetes, dyslipidemia, and hypertension. A certain population of NAFLD progresses to non-alcoholic steatohepatitis (NASH) and forms liver fibrosis due to hepatic inflammation and hepatocyte death. Thereafter, cirrhosis is induced, which can eventually lead to liver cancer and cardiovascular disease (Non-Patent Literature 1).

Definitive diagnosis of NASH is made by pathological diagnosis. Activity is scored for steatosis, inflammatory cell infiltration, and ballooning, and is classified based on the total of these scores, NAFLD activity score (NAS). Diseases are classified based on the degree of liver fibrosis. Specifically, stage 1 is pericentral fibrosis, stage 2 is periportal fibrosis, stage 3 is bridging fibrosis, and stage 4 is cirrhosis.

According to the current FDA guidance (Non-Patent Literature 2), the endpoints after phase 2 of the clinical trial must demonstrate histological improvement, i.e., either improvement of NAS or improvement of liver fibrosis.

Thiazolidinedione-based drugs and vitamin E, which are PPARγ agonists, are recommended as therapeutic agents for NASH. However, since their effects are indirect effects associated with diabetes treatment, they have not been proven to be effective in preventing the development of liver cirrhosis and liver cancer; rather, there is a great concern about side effects due to long-term administration. Thus, methods for treating NAFLD and NASH have not yet been established. For this reason, FXR agonists (obeticholic acid, Tropifexor, etc.), SCD1 inhibitors (Aramchol), ASK1 inhibitors (Selonsertib), PPARα/γ agonists (Elafibranor), and other various drugs are under development, and new therapeutic agents are desired.

CITATION LIST

Non-Patent Literature

Non-Patent Literature 1: Hepatology. 2018 January;
Non-Patent Literature 2: Noncirrhotic Nonalcoholic Steatohepatitis With Liver Fibrosis: Developing Drugs for Treatment Guidance for Industry

SUMMARY OF INVENTION

Technical Problem

An object of the present invention is to provide a therapeutic agent for fatty liver diseases.

Solution to Problem

As a result of intensive studies, the present inventors have found that a compound having a specific structure can treat fatty liver diseases, and have completed the present invention.

The present invention includes the following embodiments.

[1]
A therapeutic agent for a fatty liver disease, comprising a compound represented by the following formula (1):

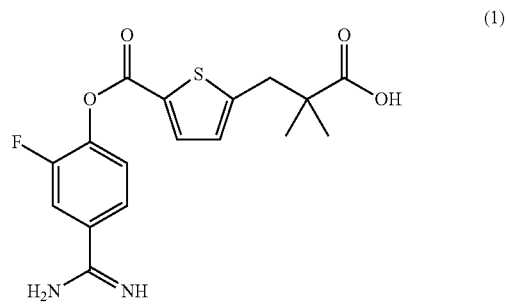 [SMILES: CC(C)(Cc1ccc(C(=O)Oc2ccc(C(=N)N)cc2F)s1)C(=O)O]

or a pharmaceutically acceptable salt thereof.

[2]
The therapeutic agent according to [1], wherein the pharmaceutically acceptable salt is hydrochloride.

[3]
The therapeutic agent according to [1] or [2], wherein the fatty liver disease is non-alcoholic fatty liver disease (NAFLD) or non-alcoholic steatohepatitis (NASH).

[4]
The therapeutic agent according to [3], wherein the fatty liver disease is NAFLD.

[5]
The therapeutic agent according to [4], wherein the NAFLD is accompanied by liver fibrosis.

[6]
The therapeutic agent according to [4], wherein the NAFLD is accompanied by liver inflammation.

[7]
The therapeutic agent according to [3], wherein the fatty liver disease is NASH.

[8]
The therapeutic agent according to [7], wherein the NASH is accompanied by liver fibrosis.

[9]
The therapeutic agent according to [7], wherein the NASH is accompanied by liver inflammation.

The above embodiments can also be expressed as follows.

[A]
A method for treating a fatty liver disease, comprising administering a therapeutically effective amount of the compound represented by the formula (1) or a pharmaceutically acceptable salt thereof defined in [1] above to a patient in need of the treatment.

[B]
The compound represented by the formula (1) or a pharmaceutically acceptable salt thereof defined in [1] above, for use in the treatment of a fatty liver disease.

[C]
Use of the compound represented by the formula (1) or a pharmaceutically acceptable salt thereof defined in [1] above, for the treatment of a fatty liver disease.

[D]

Use of the compound represented by the formula (1) or a pharmaceutically acceptable salt thereof defined in [1] above, in the production of a therapeutic agent for a fatty liver disease.

Advantageous Effect of Invention

According to the present invention, a therapeutic agent for fatty liver diseases can be provided.

BRIEF DESCRIPTION OF DRAWINGS

FIG. 1A shows plasma ALT for 12 weeks treatment of an administration substance.

FIG. 1B shows plasma ALT for 18 weeks treatment of an administration substance.

FIG. 1C shows plasma AST for 18 weeks treatment of an administration substance.

FIG. 2 shows plasma Tcho for 18 weeks treatment of an administration substance.

FIG. 3 shows liver TG for 18 weeks treatment of an administration substance.

FIG. 4 shows the Sirius red-positive area in the liver for 18 weeks treatment of an administration substance.

FIG. 5 shows the number of CD68-positive hCLS by immunostaining of the liver for 18 weeks treatment of an administration substance.

DESCRIPTION OF EMBODIMENTS

Embodiments of the present invention will be described in detail below; however, the present invention is not limited thereto, and can be modified in various ways within the range not deviated from the gist of the present invention.

An embodiment of the present invention relates to a therapeutic agent for a fatty liver disease, comprising a compound represented by the following formula (1):

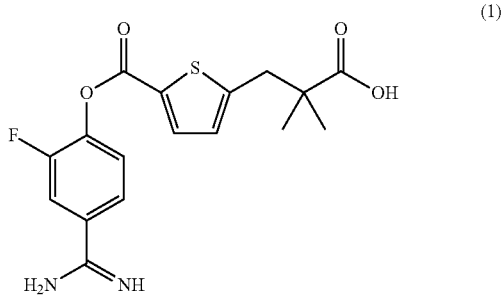 [SMILES: CC(C)(Cc1ccc(C(=O)Oc2ccc(C(=N)N)cc2F)s1)C(=O)O]

(1)

or a pharmaceutically acceptable salt thereof.

The compound represented by the formula (1) or a pharmaceutically acceptable salt thereof can be easily synthesized by a person skilled in the art with reference to, for example, the synthesis methods described in WO2015/137407 and WO2015/137408.

The pharmaceutically acceptable salt of the compound represented by the formula (1) is not particularly limited as long as it can be used as a medicament. Examples thereof include inorganic acid salts, such as hydrochloride, sulfate, nitrate, hydrobromate, and phosphate; and organic acid salts, such as fumarate, maleate, malate, tartrate, citrate, succinate, methanesulfonate, p-toluenesulfonate, lactate, acetate, and palmitate.

The compound represented by the formula (1) or a pharmaceutically acceptable salt thereof may form solvates, such as hydrates. In the present specification, solvates shall be included in the compound represented by the formula (1) or a pharmaceutically acceptable salt thereof.

The therapeutic agent of the present embodiment may only comprise the compound represented by the formula (1) or a pharmaceutically acceptable salt thereof, or may further comprise other components. Although other components appropriately differ depending on the dosage form and the like, examples thereof include excipients, binders, lubricants, disintegrants, surfactants, suspending agents, emulsifiers, preservatives, colorants, fragrances, sweetening agents, flavoring agents, stabilizers, and thickening agents.

The therapeutic agent of the present embodiment can be administered orally or parenterally. Examples of the dosage form for oral administration include tablets, pills, granules, powders, capsules, syrups, emulsions, and suspensions. Examples of the dosage form for parenteral administration include injections, infusions, drips, eye drops, and suppositories.

The therapeutic agent of the present embodiment can treat fatty liver diseases. The term "treat" in the present specification includes preventing the development of fatty liver diseases, inhibiting the progress of fatty liver diseases, relieving the symptoms of fatty liver diseases, curing fatty liver diseases, and the like.

Specific examples of fatty liver diseases include NAFLD, NASH, metabolic-associated fatty liver disease (MAFLD), and fatty liver. Although it is not particularly limited, the therapeutic agent of the present embodiment can be preferably used for the treatment of NAFLD and/or NASH.

In the treatment of fatty liver diseases, the therapeutic agent of the present embodiment can improve one or more symptoms selected from the group consisting of liver damage (e.g., increase in plasma ALT and/or AST), lipid metabolism disorders (e.g., increase in plasma total cholesterol), formation of fatty liver (e.g., increase in liver triglyceride), liver fibrosis (e.g., increase in Sirius red-positive area), and hepatitis (e.g., increase in the number of hCLS).

EXAMPLES

The present invention will be described in more detail below using Examples; however, the technical scope of the present invention is not limited thereto.

In the present Examples, using a high-fat and high-fructose-induced NASH model (fast-food diet model: FFD model), the effect of a test drug was evaluated. For the FFD model, refer to BMC Gastroenterol. 2020; 20: 210 and Am J Physiol Gastrointest Liver Physiol. 2013 Oct. 1; 305(7): G483-95.

<Administration Substance>

0.5% (w/v) methylcellulose aqueous solution (hereinafter referred to as "0.5% MC")

Test drug

The test drug was prepared by adding hydrochloride of the compound represented by the formula (1) (hereinafter referred to as "compound 1") to 0.5% MC and sonicating the mixture.

<Experimental Animal>

6-week-old C57BL/6J Jms Slc male mice were fed with standard diet (D09100304, Research Diets, Inc.) or FFD diet for pathogenesis (D09100310N, Research Diets, Inc.) for 20 weeks. Then, the mice were grouped as shown in Table 1 based on three indices, i.e., plasma alanine aminotransferase (ALT) levels, body weight, and fasting blood glucose levels.

<Administration Method>

According to the dosage and usage shown in Table 1, the administration substance was gavaged to each group for 18 weeks.

[Table 1]

TABLE 1

| Group | Group name | Fed diet | Administration substance | Dosage (compound 1) | Usage |
|---|---|---|---|---|---|
| 1 | Normal | Standard diet | 0.5% MC | — | Once in AM Once in PM |
| 2 | Vehicle | FFD diet | 0.5% MC | — | Once in AM Once in PM |
| 3 | Cpd 1 10 mg/kg QD | FED diet | Test drag 0.5% MC | 10 mg/kg/day — | Once in AM Once in PM |
| 4 | Cpd 1 30 mg/kg QD | FFD diet | Test drag 0.5% MC | 30 mg/kg/day — | Once in AM Once in PM |
| 5 | Cpd 1 60 mg/kg/day BID | FFD diet | Test drag | 60 mg/kg/day | Once in AM Once in PM |

* AM: at 9 ± 1 hour, PM: at 17 ± 1 hour
* Groups 3 to 5 are also referred to as "compound 1 (10) group," "compound 1 (30) group," and "compound 1 (60) group," respectively.

<Evaluation Method>

ALT was measured by collecting blood from the tail vein after 12 weeks of administration. An autopsy was performed after 18 weeks of administration, and plasma aspartate aminotransferase (AST), plasma total cholesterol (Tcho), and liver triglyceride (TG) were measured. In addition, the Sirius red-positive area and the number of hepatic crown-like structures (hCLS) were measured by liver pathological analysis.

<Statistical Analysis>

Statistical analysis was performed using GraphPad Prism 6 (GraphPad Software, Inc.). For the Normal group and the Vehicle group, t-test or Mann-Whitney's test was performed. For the Vehicle group and the compound 1 group, Dunnett' multiple comparison test or Dunn's multiple comparison test was performed. Any of the test methods was appropriately selected according to the distribution of each parameter. The significance level of all the tests was set to p=0.05.

<Plasma ALT and AST>

FIG. 1A shows plasma ALT after 12 weeks of administration, FIG. 1B shows plasma ALT after 18 weeks of administration, and FIG. 1C shows plasma AST after 18 weeks of administration. The Vehicle group showed statistically significant increases in plasma ALT and AST in comparison with the Normal group. The compound 1 (60) group showed a statistically significant inhibitory effect on the increases in plasma ALT and AST in comparison with the Vehicle group. The results confirmed that the compound 1 improved liver damage.

<Plasma Tcho>

FIG. 2 shows plasma Tcho values after 18 weeks of administration. The Vehicle group showed a statistically significant increase in plasma Tcho in comparison with the Normal group. The compound 1 (60) group showed a statistically significant inhibitory effect on the increase in plasma Tcho in comparison with the Vehicle group. The results confirmed that the compound 1 improved lipid metabolism.

<Liver TG>

A liver sample was homogenized in a phosphate buffer and extracted with methanol and chloroform overnight. Then, chloroform and distilled water were further added thereto. The mixture was separated by centrifugation, the chloroform layer was collected, and the solvent was dried. The precipitate was dissolved in isopropanol/TritonX-100, and this was used as a measurement sample, the measurement was carried out using Triglyceride E-Test Wako (FUJIFILM Wako Pure Chemical Corporation).

FIG. 3 shows liver TG values after 18 weeks of administration. The Vehicle group showed a statistically significant increase in liver TG in comparison with the Normal group. The compound 1 (30) group and the compound 1 (60) group showed a statistically significant inhibitory effect on the increase in liver TG in comparison with the Vehicle group. The results confirmed that the compound 1 had an inhibitory effect on hepatic steatosis.

<Sirius Red-Positive Area>

The excised liver was fixed in a 10% neutral buffered formalin solution, and embedded in paraffin and Sirius red-stained specimens were prepared according to standard methods. The Sirius red-stained specimen was used to calculate the positive area. The positive area of the Normal group was averaged and used as the background.

FIG. 4 shows the Sirius red-positive area in the liver after 18 weeks of administration. The Vehicle group showed a statistically significant increase in the Sirius red-positive area in the liver in comparison with the Normal group. The compound 1 (60) group showed a statistically significant inhibitory effect on the increase in the Sirius red-positive area in the liver in comparison with the Vehicle group. The results confirmed that the compound 1 had antifibrotic effect on the liver.

<Number of hCLS>

A CD68 immunostaining specimen (rabbit anti-CD68 polyclonal antibody [ab125212], Abcam) was prepared, and the number of hCLS was counted.

FIG. 5 shows the number of CD68-positive hCLS using immunostaining of the liver after 18 weeks of administration. The Vehicle group showed a statistically significant increase in the number of hCLS in the liver in comparison with the Normal group. The compound 1 (10) group and the compound 1 (60) group showed a statistically significant inhibitory effect on the increase in the number of hCLS in the liver in comparison with the Vehicle group. The results confirmed that the compound 1 had anti-inflammatory effect on the liver.

<Pathological Analysis>

Table 2 shows histopathological findings of the liver. The pathological analysis also confirmed that the compound 1 had effects of improving steatosis and fibrosis in the liver.

[Table 2]

TABLE 2

| | histopathological findings | | | | |
|---|---|---|---|---|---|
| | | Group | | | |
| | Normal | Vehicle | Cpd 1 10 mg/kg QD | Cpd 1 30 mg/kg QD | Cpd 1 60 mg/kg/day BID |
| | Number of mice evaluated | | | | |
| | 8 | 8 | 8 | 8 | 8 |
| Fat formation: large fat droplets | | | | | |
| − | 8 | | | | |
| ± | | | 3 | 4 | 2 | 7 |
| + | | | 5 | 4 | 6 | 1 |
| Fibrosis | | | | | |
| − | 8 | | | | |
| ± | | | 3 | 6 | 6 | 6 |
| + | | | 5 | 2 | 1 | 2 |

Notes)
−: negative/within normal limit,
±: Slight,
+: Moderate,
++: Marked
For fibrosis assessment, individuals with liver nodules were excluded <Comprehensive Evaluation>

The compound 1 inhibited the increases in plasma ALT/AST/Tcho and liver TG, and thus significantly improved fatty liver disease-related indicators (hepatic enzymes and lipid metabolism). Further, the compound 1 significantly suppressed the Sirius red-positive area and the number of hCLS, and improved indices of liver fibrosis and inflammation. The histopathological findings also showed results supporting these improvement effects. From the above results, the efficacy of the compound 1 in the NASH model was confirmed.

The invention claimed is:

1. A method for treating a fatty liver disease, comprising administering a therapeutically effective amount of a compound represented by the following formula (1):

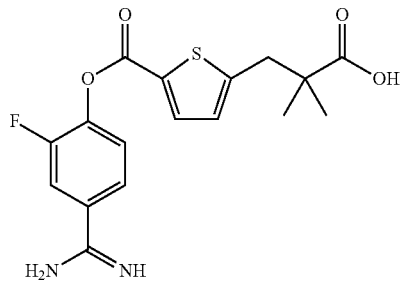

(1)

or a pharmaceutically acceptable salt thereof, to a patient in need thereof,
wherein the fatty liver disease is selected from the group consisting of non-alcoholic fatty liver disease (NAFLD), non-alcoholic steatohepatitis (NASH) and metabolic-associated fatty liver disease (MAFLD).

2. The method according to claim 1, wherein the pharmaceutically acceptable salt is hydrochloride.

3. The method according to claim 1, wherein the fatty liver disease is non-alcoholic fatty liver disease (NAFLD) or non-alcoholic steatohepatitis (NASH).

4. The method according to claim 3, wherein the fatty liver disease is NAFLD.

5. The method according to claim 4, wherein the NAFLD is accompanied by liver fibrosis.

6. The method according to claim 4, wherein the NAFLD is accompanied by liver inflammation.

7. The method according to claim 3, wherein the fatty liver disease is NASH.

8. The method according to claim 7, wherein the NASH is accompanied by liver fibrosis.

9. The method according to claim 7, wherein the NASH is accompanied by liver inflammation.

10. The method according to claim 1, wherein a therapeutically effective amount of the compound of formula (1) or a pharmaceutically acceptable salt thereof is administered orally.

11. The method according to claim 1, wherein a therapeutically effective amount of the compound of formula (1) or a pharmaceutically acceptable salt thereof is administered parentally.

* * * * *

UNITED STATES PATENT AND TRADEMARK OFFICE
CERTIFICATE OF CORRECTION

PATENT NO. : 12,023,320 B2
APPLICATION NO. : 18/171126
DATED : July 2, 2024
INVENTOR(S) : Ayatoshi Ando et al.

It is certified that error appears in the above-identified patent and that said Letters Patent is hereby corrected as shown below:

In the Specification

In Column 5, Table 1, Group 3 Administration substance, "drag" should read -- drug --.

In Column 5, Table 1, Group 4 Administration substance, "drag" should read -- drug --.

In Column 5, Table 1, Group 5 Administration substance, "drag" should read -- drug --.

Signed and Sealed this
Third Day of September, 2024

Katherine Kelly Vidal
*Director of the United States Patent and Trademark Office*